United States Patent [19]

Laughlin

[11] Patent Number: 4,655,233
[45] Date of Patent: Apr. 7, 1987

[54] DENTAL FLOSSING TOOL

[76] Inventor: Patrick E. Laughlin, 1191 Beechwood Dr., Green Bay, Wis. 54303

[21] Appl. No.: 794,774

[22] Filed: Nov. 4, 1985

[51] Int. Cl.[4] .............................................. A61C 15/00
[52] U.S. Cl. ...................................................... 132/91
[58] Field of Search ................ 433/141; 132/91, 92 R

[56] References Cited

U.S. PATENT DOCUMENTS

| | | | |
|---|---|---|---|
| 788,947 | 5/1905 | Roth | 132/91 |
| 2,873,749 | 2/1959 | Gjerde | 132/91 |
| 4,253,477 | 3/1981 | Eichmann | 132/91 |

Primary Examiner—Robert Peshock
Attorney, Agent, or Firm—Russell L. Johnson

[57] ABSTRACT

This invention is related to a tool for the dental flossing of teeth and a precut length of dental floss having gripping attachments secured to the ends of the length of floss. The precut length(s) of floss are configured so as to facilitate the gripping of the attachments by the flossing tool. The tool is fully operable by the use of one hand.

5 Claims, 9 Drawing Figures

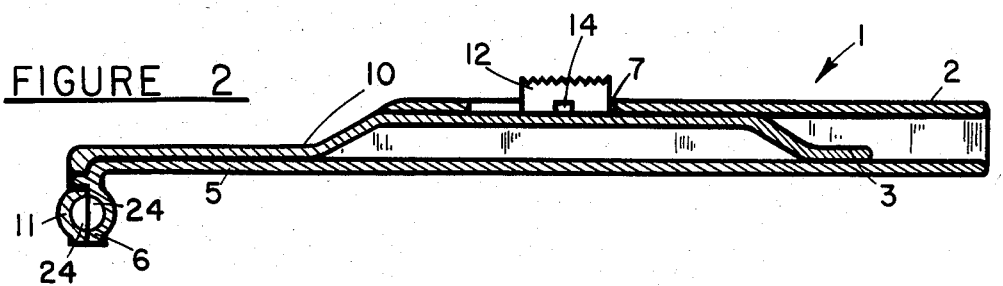
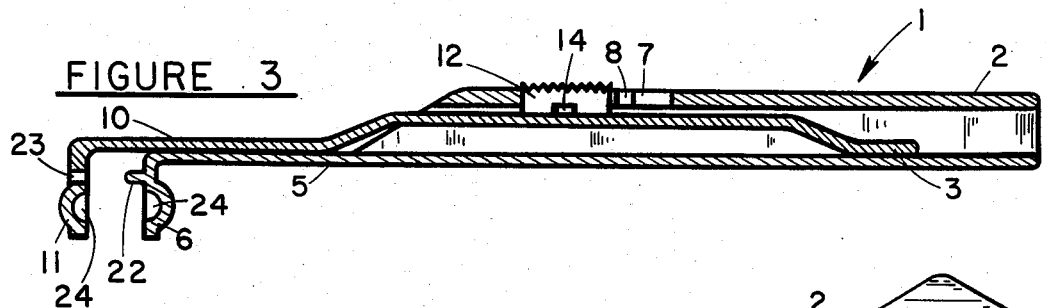
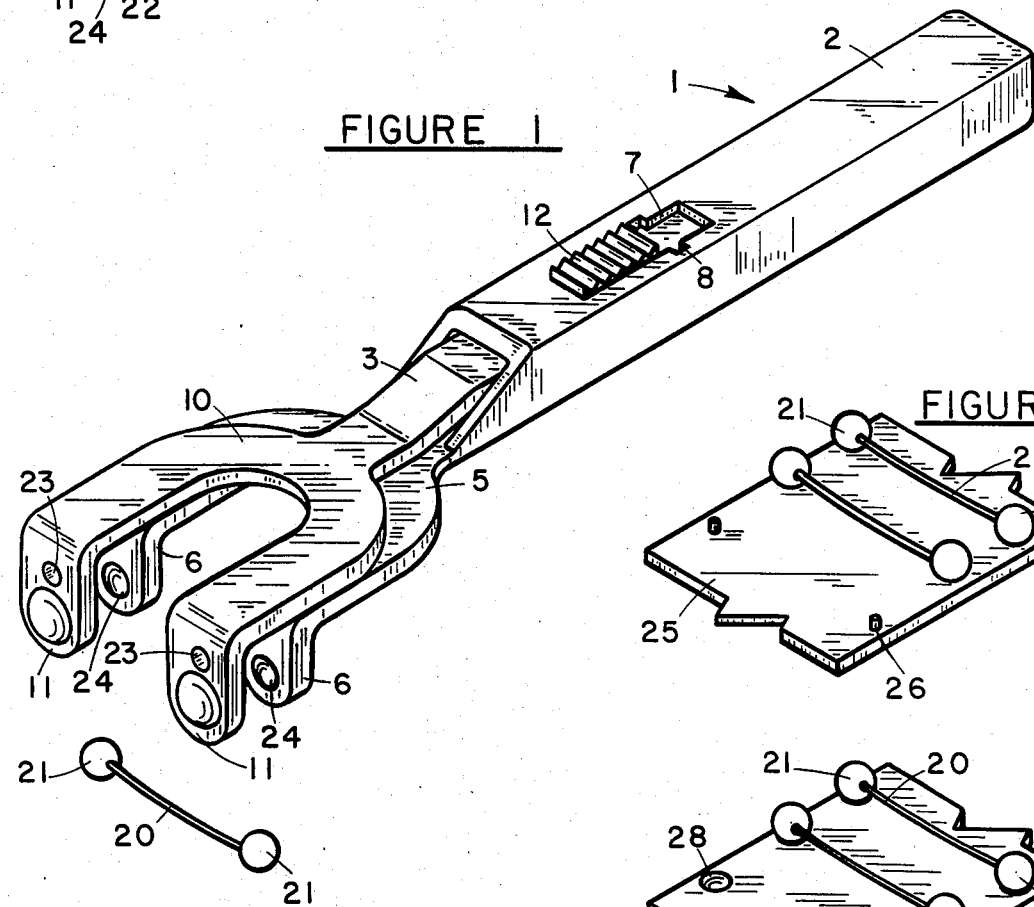
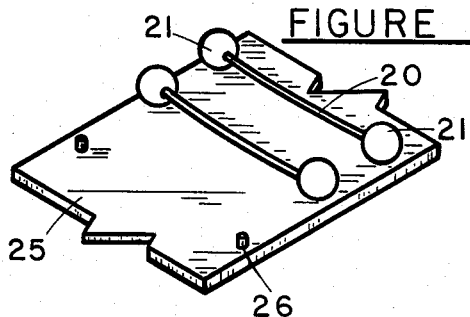
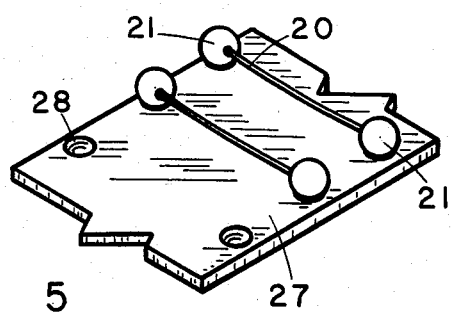

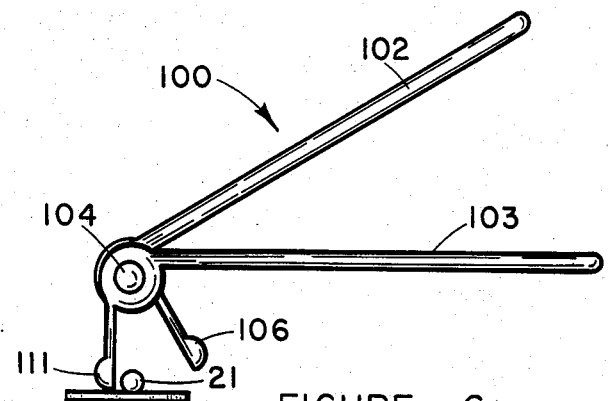
FIGURE 6
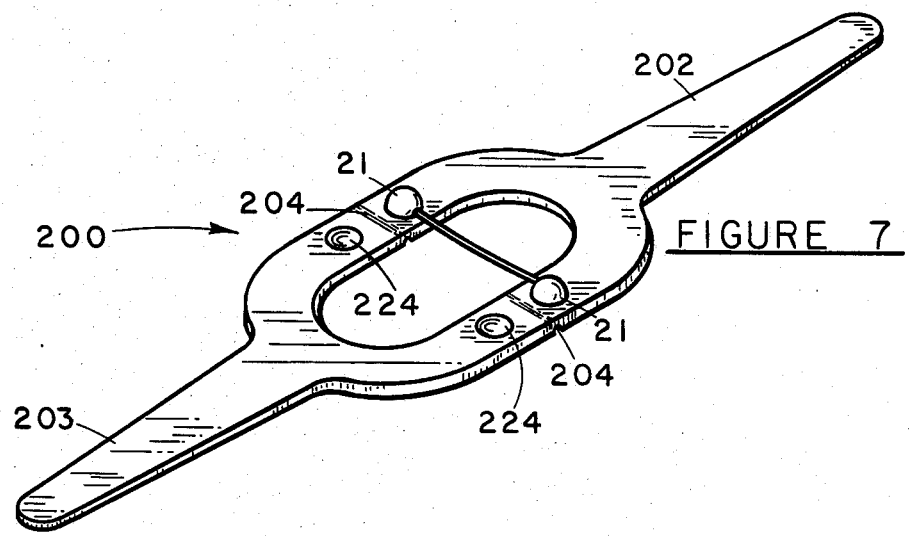
FIGURE 7
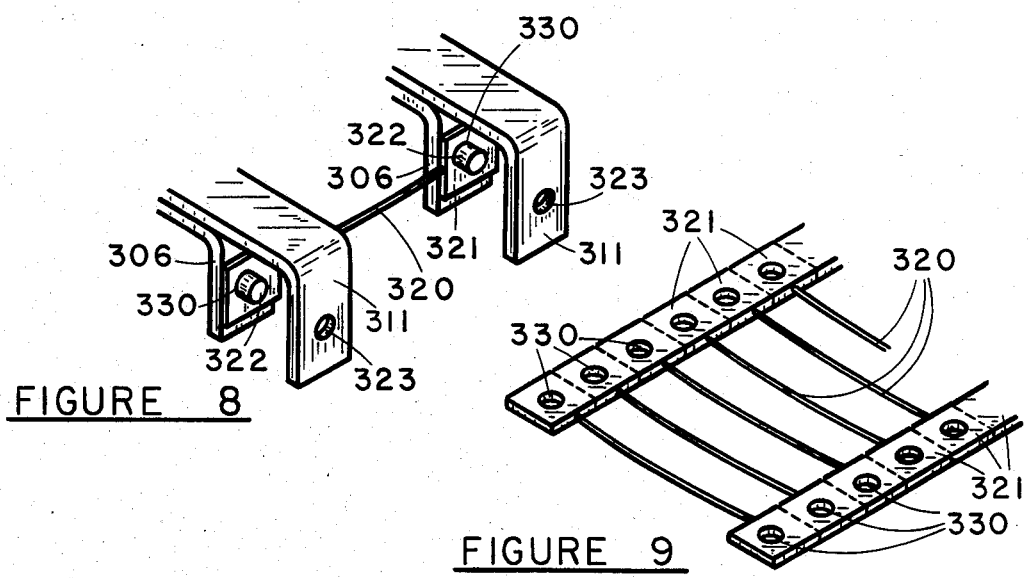
FIGURE 8
FIGURE 9

DENTAL FLOSSING TOOL

FIELD OF THE INVENTION

This invention relates to tools for holding dental floss for the flossing of teeth.

More particularly this invention relates to tools for the flossing of teeth wherein the tool is configured so as to permit the tool to secure a precut length of dental floss.

Still more particularly this invention relates to a flossing tool which is operable by persons who have impaired use of the hands or have only one hand or who have mechanical prostheses as replacements for missing hands.

BACKGROUND OF THE INVENTION

The flossing of teeth is an essential part of dental hygiene. Many people, for a variety of reasons, cannot floss satisfactorily by manipulating the floss with their fingers. There are presently available a variety of flossing tools that satisfactorily facilitate the flossing of teeth for the general population. These flossing tools ordinarily require some manipulative skills in attaching and detaching the floss. Persons who have impaired use or the loss of one or even both hands have difficulty or are unable to change the floss in most, if not all, of the presently available floss holding tools. It, therefore, becomes necessary for them to secure the assistance of another person to replace the floss in the holder.

OBJECTS

It is an object of this invention to provide a dental flossing tool wherein the dental floss may be readily changed by a person who suffers impairment of the use or the loss of one or both hands.

It is further an object of this invention to provide precut floss elements associable with a dispenser which cooperates with the above described tool to permit such an impaired person to readily change the floss in the tool with outside assistance.

It is further an object of this invention to provide the above described tool and precut floss in a form that is economical to produce and durable and functional in use.

Other objects will become apparent from the following specifications, claims, and drawings.

BRIEF DISCUSSION OF THE PRIOR ART

The prior art teaches the use of precut lengths of dental floss in U.S. Pat. Nos. 2,180,522, and 2,187,899 to HENNE. The patent art also teaches the use of reusable tools for holding dental floss. U.S. Pat. No. 2,870,772 to PARKS JR. is a typical example.

In this patent application the inventor does not wish to suggest that he is the inventor of precut lengths of dental floss nor does he wish to suggest that he is the inventor of reusable tools for dental flossing.

The term "secure" as used herein shall be read to mean "free from risk of loss".

The novelty of the instant invention is seen as residing in the provision of a tool that securely grasps and holds precut lengths of dental floss. More particularly the invention provides one with limited manipulative capabilities with a means for securing a precut length of dental floss to a flossing tool and after use, the means for replacing the used length of floss. The prior art of which the applicant is aware does not provide a means by which an arthritic or an amputee or the like can load and change the floss in a flossing tool without the aid of another person.

BRIEF DESCRIPTION OF THE INVENTION

The invention in its simplest form comprises a precut length of dental floss having gripping elements attached to the ends of the length of floss, a bifurcated flossing tool having grippers for grasping and releasing the gripping elements of the precut length of dental floss, and the tool is configured so that the grippers are readily operable by a person having very limited manipulative capability.

BRIEF DESCRIPTION OF THE DRAWINGS

FIG. 1 is a pictorial view of the tool of this invention and a precut length of dental floss having gripping beads.

FIG. 2 is a sectioned side elevational view of the tool of FIG. 1 showing the gripping jaws in the closed position.

FIG. 3 is the view of FIG. 2 showing the gripping jaws open.

FIG. 4 is a pictorial view of a precut length of floss positioned on a pin dispenser.

FIG. 5 is a view similar to FIG. 4 wherein the dispenser is adhesive.

FIG. 6 is an elevational view of an embodiment of the tool wherein the jaws are pivoted.

FIG. 7 is a pictorial view of an embodiment of the tool wherein the tool body is a one piece unit.

FIG. 8 is a fragmentary pictorial view of gripper jaws similar to those of FIGS. 1 through 3 wherein the jaws are configured to receive a tape type gripping means.

FIG. 9 is a pictorial view of a supply of precut floss having gripping attachments suitable for use with the jaw configurations illustrated in FIG. 8.

DETAILED DESCRIPTION OF THE INVENTION

In the figures like numbers refer to like objects.

Referring now to FIGS. 1 through 3. Flossing tool 1 comprises an outer sleeve member 2 and a sliding member 3. Outer sleeve member 2 has as a part of its construction bifurcated support 5 having depending therefrom fixed jaws 6. Outer sleeve member 2 is further provided with guide and latch opening 7 having detent notch 8 as a part thereof. Sliding member 3 has as a part of its construction bifurcated support 10 having depending therefrom movable jaws 11. Sliding member 3 is further provided with mover 12 which, when at assembly with sleeve member 2, projects through guide and latch opening 7.

Tool 1 is configured so as to be manipulatable by the use of one hand or by a mechanical prosthesis and can be readily operated even by one with diminished manipulative capabilities such as an arthritic or one with several missing fingers. To close jaws 6 and 11 from the position shown in FIGS. 1 and 3 to the position shown in FIG. 2, mover 12 is slid back in guide and latch opening 7 until jaws 6 and 11 are closed and detent pin 14 snaps into detent notch 8 thereby locking jaws 6 and 11 in the closed position. To open jaws 6 and 11 mover 12 is pressed downward until detent pin 14 is disengaged from detent notch 8 and mover 12 is then pushed forward thereby opening jaws 6 and 11.

Precut dental floss 20 is provided at each end with gripping members 21. Gripping members 21 are configured so as to index into jaws 6 and 11 so as to be securely held thereby when jaws 6 and 11 are in the closed position.

For proper flossing the floss must be taut enough in the tool so that the floss can be worked between the teeth but possess enough slack so that the floss can wrap the mesial and distal aspects of the teeth to properly clean those surfaces of the teeth with a few strokes. When flossing, considerable tension is placed on the floss from time to time. To guard against jaws 6 and 11 becoming misaligned or forced open at such times, jaws 6 are provided with indexing pins 22 and jaws 11 are provided with mating pin seats 23. As shown in FIGS. 1 through 5, floss 20 is provided with spherical gripping members 21. Jaws 6 and 11 of tool 1 are provided with hemispherical gripping seats 24. As illustrated in FIG. 1 a precut dental floss 20 having gripping members 21 may be removed from a supply of such assemblies and placed upon a surface as shown. Jaws 6 and 11 of tool 1 are then positioned on each side of gripping members 21 and jaws 6 and 11 are closed thereby drawing gripping members 21 into hemispherical seats 24. In so doing floss 20 is given the proper degree of tension for proper flossing.

As illustrated in FIGS. 4 and 5, floss 20 with gripping members 21 attached may be carried on a dispenser to facilitate the positioning of gripping members 21 for pick up in jaws 6 and 11.

In FIG. 4 dispenser 25 is provided with pins 26 which fit in recesses (not shown) in gripping members 21. In FIG. 5, dispenser 27 is provided with small adhesive spots 28 to which gripping members 21 may be detachably adhered.

Many variants of tool 1 and precut floss 20 may be had without departing from the scope of this invention. The utility and the manipulative ease of loading and unloading tool may benefit those with normal manipulative skills.

Referring now to FIG. 6. FIG. 6 illustrates a tool 100 which has a plier-like pivot 104 such that when handles 102 and 103 are brought together jaws 106 and 111 close upon and grip gripping member 21 in much the same fashion as disclosed with relation to tool 1 of FIGS. 1 through 5.

Referring now to FIG. 7. Tool 200 is hinged at 204 and is provided with hemispherical gripping seats 224 into which gripping members 21 may be placed. When handles 202 and 203 are rotated on hinge 204 seats 224 are brought together and gripping member 21 is securely grasped in tool 200.

It can be seen from FIGS. 1, 6, and 7 that there are possible several embodiments of a tool for gripping precut lengths of floss having gripping members secured at the end of the precut lengths of floss so that the precut lengths of floss may be gripped by and released from the tool by a user of the tool having very limited manipulative capabilities. In a like manner several embodiments of the precut length of floss having gripping members are practicable.

Refering now to FIGS. 8 and 9. Jaws 306 and 311 are similar in operation to jaws 6 and 11 of FIGS. 1, 2, and 3. Pins 322 engage pin seats 323 in much the same fashion as pins 22 and seats 23 of FIGS. 1, 2, and 3. Precut floss 320 is similar to floss 20. Gripping means 321, while performing many of the same functions as gripping means 21, represents a separate embodiment of this portion of the instant invention.

In practice, a precut length of dental floss 320 may be taken from a supply of such assemblies and hole 330 in gripping means 321 may be mounted to pins 322 of jaws 306. Thereafter jaws 306 and 311 are closed, thereby securing gripping means 321 between jaws 306 and 311.

The inventor has provided enabling disclosures of the preferred embodiments of his invention. He has disclosed the best modes of practicing the invention known to him at the time of preparation of this specification. However, it should be understood that the scope of the invention should not be limited to the disclosed embodiments but rather the scope of the invention should only be limited by the scope of the appended claims and all equivalents thereto which would become obvious to one skilled in the art.

I claim:

1. A tool for the dental flossing of teeth comprising; an elongate tool having a bifurcated floss gripping end and a handle end and the floss gripping end is configured so as to receive and securely hold a precut length of floss, the precut length of floss having secured to its ends gripping attachments which permit the precut length of floss to be securely gripped by the floss gripping end of the tool and the tool is provided with opening and closing means for grippers on the floss gripping end of the tool and the tool and the opening and closing means is operable by the use of one hand, and wherein the grippers are provided with hemispherical cavities in each gripping jaw of the two pairs of gripping jaws and the hemispherical cavities are positioned so that the hemispherical cavities open towards each other when the opening and closing means for the grippers is in the open position permitting the positioning between each of the pairs of gripping jaws a spherical gripping attachment and the hemispherical cavities are closed upon the spherical gripping attachment when the opening and closing means is in the closed position so as to permit the jaws to be employed to pick up and securely grasp a precut length of dental floss having spherical gripping attachments secured at each end of the length of dental floss.

2. A tool for the dental flossing of teeth comprising; an elongate tool having a bifurcated floss gripping end and a handle end and the floss gripping end is configured so as to receive and securely hold a precut length of floss, the precut length of floss having secured to its ends gripping attachments which permit the precut length of floss to be securely gripped by the floss gripping end of the tool and the tool is provided with opening and closing means for grippers on the floss gripping end of the tool and the tool and the opening and closing means is operable by the use of one hand, and wherein the grippers are provided with a pin and pin seat means for gripping a precut length of dental floss and the precut length of floss has had gripping attachments secured at each end of the length of floss the gripping attachments define holes which will pass over the pins provided to the grippers.

3. A tool for the dental flossing of teeth comprising; an elongate tool having a bifurcated floss gripping end and a handle end and the floss gripping end is configured so as to receive and securely hold a precut length of floss, th e precut length of floss having secured to its ends gripping attachments which permit the precut length of floss to be securely gripped by the floss gripping end of the tool and the tool is provided with opening and closing means for grippers on the floss gripping end of the tool and the tool and the opening and closing means is operable by the use of one hand, and wherein the tool comprises a two ended sleeve member having a tubular sleeve forming one end and a bifurcated support means forming the other end and each of the bifurcations has projecting from its end a jaw and the jaw is provided with a first gripping means which cooperates with a second gripping means associated with mating jaws on sliding member to form a means for gripping the gripping attachments of a precut length of dental floss and the sliding member is a two ended sliding member having one end formed as a slide which is movable within the tubular sleeve of the sleeve member and the other end is formed as a bifurcated support means and each of the bifurcations has projecting from its ends a jaw and the jaw is provided with the second gripping means which cooperates with the first gripping means in gripping and releasing the gripping attachments of a precut length of dental floss and the sleeve member and sliding member are provided with a releasable detent means for locking the sliding member to the tubular member when the jaws of the tool are closed.

4. A tool for the dental flossing of teeth comprising; an elongate tool having a bifurcated floss gripping end and a handle end and the floss gripping end is configured so as to receive and securely hold a precut length of floss, the precut length of floss having secured to its ends gripping attachments which permit the precut length of floss to be securely gripped by the floss gripping end of the tool and the tool is provided with opening and closing means for grippers on the floss gripping end of the tool and the opening and closing means is operable by the use of one hand and wherein the tool comprises; a plier assembly having two elongate members pivoted to each other in their midspan and the ends to one side of the pivot form opening and closing handles and the ends to the other side of the pivot form bifurcated support means having formed at the ends of the bifurcations jaws configured to grip the gripping attachments at the end of the precut length of dental floss.

5. A tool for the dental flossing of teeth comprising; an elongate tool having a bifurcated floss gripping end and a handle end and the floss gripping end is configured so as to receive and securely hold a precut length of floss, the precut length of floss having secured to its ends gripping attachments which permit the precut length of floss to be securely gripped by the floss gripping end of the tool and the tool is provided with opening and closing means for grippers on the floss gripping end of the tool and the opening and closing means is operable by the use of one hand and wherein the tool comprises a one piece elongate construction which is symetrical about a longitudinal handle axis and a transverse hinge axis and the one piece tool has a widened portion about the intersection of the longitudinal handle axis and the transverse hinge axis and the widened portion defines a hole centered on the intersection and the widened section has projecting therefrom and along the longitudinal handle axis, handle segments and the widened section has gripping means in the portion of the widened section to either side of the hole in the direction of the hinge axis and positioned a short distance lateral to the hinge axis and gripping means is configured so as to receive the gripping attachment of the precut length of dental floss and when the portion of the tool to one side of the hinge axis is pivoted about the hinge axis so as to bring it into contact with the portion of the tool to the other side of the hinge axis the gripping attachments of precut length of dental floss is securely gripped in the tool.

* * * * *